(12) United States Patent
Hartley et al.

(10) Patent No.: US 8,911,488 B2
(45) Date of Patent: Dec. 16, 2014

(54) THORACIC INTRODUCER

(75) Inventors: David E. Hartley, Wannanup (AU);
Timothy A. Chuter, San Francisco, CA (US); Roy K. Greenberg, Bratehahl, OH (US)

(73) Assignees: The Cleveland Clinic Foundation, Cleveland, OH (US); Cook Medical Technologies LLC, Bloomington, IN (US)

( * ) Notice: Subject to any disclaimer, the term of this patent is extended or adjusted under 35 U.S.C. 154(b) by 673 days.

(21) Appl. No.: 13/059,499

(22) PCT Filed: Aug. 24, 2009

(86) PCT No.: PCT/US2009/004807
§ 371 (c)(1),
(2), (4) Date: Jun. 6, 2011

(87) PCT Pub. No.: WO2010/024869
PCT Pub. Date: Mar. 4, 2010

(65) Prior Publication Data
US 2011/0230947 A1    Sep. 22, 2011

Related U.S. Application Data

(60) Provisional application No. 61/190,142, filed on Aug. 26, 2008.

(51) Int. Cl.
| | | |
|---|---|---|
| *A61F 2/06* | (2013.01) | |
| *A61M 25/09* | (2006.01) | |
| *A61M 29/00* | (2006.01) | |
| *A61F 2/07* | (2013.01) | |
| *A61F 2/95* | (2013.01) | |
| *A61M 25/06* | (2006.01) | |

(52) U.S. Cl.
CPC *A61M 25/09* (2013.01); *A61F 2/07* (2013.01); *A61F 2002/9517* (2013.01); *A61M 2025/0681* (2013.01); *A61F 2/95* (2013.01); *A61M 29/00* (2013.01)
USPC ....................................................... 623/1.12

(58) Field of Classification Search
CPC .................................... A61F 2/95–2/97; A61F 2002/9505–2002/9665
See application file for complete search history.

(56) References Cited

U.S. PATENT DOCUMENTS 4,586,923 A * 5/1986 Gould et al. ................ 604/95.04
4,588,399 A * 5/1986 Nebergall et al. ............. 604/529
(Continued)

FOREIGN PATENT DOCUMENTS

| WO | WO2007/082189 | 7/2007 |
| WO | WO2007/092276 | 8/2007 |

(Continued)

OTHER PUBLICATIONS

International Search Report and Written Opinion for PCT/US2009/004807 dated Nov. 11, 2009, 18 pgs.

(Continued)

*Primary Examiner* — Katherine Dowe
*Assistant Examiner* — Jonathan Hollm
(74) *Attorney, Agent, or Firm* — Brinks Gilson & Lione (57) ABSTRACT

A stent graft delivery device (30) has a pull wire arrangement with a pull wire (46) fastened to the distal end of a nose cone dilator (45) and extending to a wire pull mechanism (60) for the pull wire associated with a handle (52) of the stent graft delivery device. The pull wire can be pulled by the wire pull mechanism to induce a curve in a guide wire catheter (44) distally of the nose cone dilator such that the proximal end of the delivery device more closely fits the shape of a portion of the vasculature of a patient into which the device is deployed.

14 Claims, 4 Drawing Sheets

(56) References Cited

U.S. PATENT DOCUMENTS

| | | | |
|---|---|---|---|
| 5,203,777 A * | 4/1993 | Lee | 604/529 |
| 5,693,083 A * | 12/1997 | Baker et al. | 623/1.11 |
| 6,126,633 A | 10/2000 | Kaji et al. | |
| 6,126,649 A * | 10/2000 | VanTassel et al. | 604/528 |
| 6,475,226 B1 * | 11/2002 | Belef et al. | 606/185 |
| 7,553,323 B1 * | 6/2009 | Perez et al. | 623/1.11 |
| 2003/0018343 A1 * | 1/2003 | Mathis | 606/108 |
| 2004/0064042 A1 * | 4/2004 | Nutting et al. | 600/435 |
| 2004/0106974 A1 | 6/2004 | Greenberg et al. | |
| 2004/0193252 A1 * | 9/2004 | Perez et al. | 623/1.23 |
| 2004/0267348 A1 * | 12/2004 | Gunderson et al. | 623/1.12 |
| 2006/0155358 A1 * | 7/2006 | LaDuca et al. | 623/1.11 |
| 2008/0114440 A1 | 5/2008 | Hlavka et al. | |

FOREIGN PATENT DOCUMENTS

| | | |
|---|---|---|
| WO | WO2008/013777 | 1/2008 |
| WO | WO2008/112399 | 9/2008 |

OTHER PUBLICATIONS

Response to Written Opinion in PCT/US2009/004807 dated May 11, 2010, 3 pgs.

International Preliminary Report on Patentability for PCT/US2009/004807 dated Aug. 23, 2010, 8 pgs.

Response to European formalities requirements dated Nov. 11, 2010, 5 pgs.

* cited by examiner

Fig 5

THORACIC INTRODUCER

RELATED APPLICATIONS

The present patent document is a §371 filing based on PCT Application Serial No. PCT/US2009/004807, filed Aug. 24, 2009 (and published as WO 2010/024869A1 on Mar. 4, 2010), designating the United States and published in English, which claims the benefit of the filing date under 35 U.S.C. §119(e) of Provisional U.S. Patent Application Ser. No. 61/190,142, filed Aug. 26, 2008. All of the foregoing applications are hereby incorporated by reference in their entirety.

TECHNICAL FIELD

This invention relates to a medical device and more particularly to a medical device for the introduction of vascular devices into the body of a human or animal.

BACKGROUND ART

In recent years endovascular implantable devices have been developed for treatment of aortic aneurysms. These devices are delivered to the treatment site through the vascular system of the patient rather than by open surgery. The devices include a tubular shape of graft material such as woven Dacron, polyester polytetrafluoroethylene or the like to which is secured a tubular or cylindrical framework or scaffolding of one or more stents. The devices are initially reduced to a small diameter, placed into the leading or proximal end of a catheter delivery system whereafter the delivery system is inserted into the vascular system of the patient such as through a femoral incision. The leading end of the delivery system is maneuvered to the treatment site over a previously positioned guide wire.

Through manipulation of a control system that extends to the proximal end of the catheter from the distal end of the system outside the patient, the implantable device is deployed by holding the device at its location and withdrawing a surrounding sheath. The stent graft or implantable device can then be released and self expand or be expanded through the use of a balloon which is introduced with the stent graft introducible device. The stent graft becomes anchored into position to healthy wall tissue in the aorta (such as by barbs) whereafter the delivery system is removed leaving the device in position for reversing an aneurysm in the aorta. All blood flow is channeled through the stent graft so that no blood flow enters the aneurysm thereafter. As a result not only does the aneurysm no longer continue to grow and possibly rupture but the aneurysm actually begins to shrink and commonly disappears entirely.

For treatment of thoracic aortic aneurysms in particular it is necessary to introduce the implantable device high up in the aorta and in a region of the aorta which is curved and where there can be strong blood flow.

There has also been proposed the use of side arms in the thoracic arch region of the aorta to span between the implantable device and the great branch vessels of the thoracic arch to ensure flow to these vessels. If an implantable device which is essentially a tube is deployed in the thoracic arch without side branches then loss of blood flow to these great branch vessels could cause serious consequences to a patient.

The great vessels are essentially on the outer side of the curve of the thoracic arch. The delivery device for the implantable device, being formed from a resilient material, when extended up into the thoracic arch will essentially form the largest diameter curve it can and hence it will lie in the aorta on the side of the greatest arch. The delivery device will therefore lie close to the great vessels and there will be little or no working space to catheterize the branch vessels from the implantable device or to catheterize fenestrations in the implantable device from the branch vessels. Slight misalignment between the fenestrations in the implantable device and the branch vessels could cause significant problems in catheterization.

It is desirable therefore that a deployment device or deployment system is provided in which the proximal end of the device, the end in the thoracic arch, takes up a lesser diameter of curvature so that some working space is provided on the outer side of the curve of the thoracic arch during the introduction process.

It is the object of this invention to provide a device which will overcome at least some of these problems or at least provide the physician with a useful alternative.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

Throughout this discussion the term "stent graft" is intended to mean a device which has a tubular body of biocompatible graft material and at least one stent fastened to the tubular body to define a lumen through the stent graft. The stent graft may be bifurcated and have fenestrations, side arms or the like. Other arrangements of stent grafts are also within the scope of the invention.

DISCLOSURE OF THE INVENTION

According to a first aspect of the present invention, there is provided a stent graft delivery device comprising:

a nose cone dilator at a proximal end of the device, a resilient guide wire catheter extending from a distal end of the device to and through the nose cone dilator, a pusher catheter extending from the distal end of the device towards the proximal end, a stent graft retained on the delivery device between the distal end of the nose cone dilator and the pusher catheter, the stent graft having a graft lumen therethrough and wherein the guide wire catheter extends through the graft lumen, and the pusher catheter, a pull wire fastened at or adjacent the distal end of the nose cone dilator such that when the guide wire catheter is curved during deployment the pull wire is fastened on the inside of the curve, said pull wire extending distally and through the stent graft lumen and the pusher catheter towards distal end of the device, and a wire pull mechanism at or adjacent the distal end of the device operable to pull the pull wire to induce a curve in the guide wire catheter distally of the nose cone dilator.

As a result, the proximal end of the delivery device more closely fits the shape of a portion of the vasculature of a patient into which the device is deployed.

According to a further embodiment, there is provided a stent graft delivery device comprising a handle at a distal end, a nose cone dilator at a proximal end, the nose cone dilator including a distal end, a guide wire catheter extending from the handle to and through the nose cone dilator at the proximal end, the guide wire catheter being constructed from a resilient and flexible material, a pusher catheter extending from the handle towards the proximal end, a stent graft retained on the delivery device between the distal end of the nose cone dilator and the pusher catheter, the stent graft having a graft lumen therethrough and the guide wire catheter extending through the graft lumen, a pusher lumen through the pusher catheter, the guide wire catheter extending through the pusher lumen and able to move longitudinally and rotationally with respect to the pusher, a pull wire fastened to the distal end of the nose cone dilator and the pull wire extending distally and adjacent to and outside the guide wire catheter and through the stent graft lumen and the pusher lumen to the handle and a wire pull mechanism for the pull wire associated with the handle, whereby the pull wire can be pulled by the wire pull mechanism to induce a curve in the guide wire catheter distally of the nose cone dilator such that the proximal end of the delivery device more closely fits the shape of a portion of the vasculature of a patient into which the device is deployed.

Preferably the nose cone dilator is formed from a radiopaque material. The radiographic marking may comprise the nose cone dilator being of a selected transverse profile whereby in a selected rotational orientation the nose cone dilator can be observed by radiographic means during an endovascular procedure to be in a selected rotational orientation. For instance the nose cone dilator can be formed from a radiopaque material and the radiographic marking can comprise a transverse notch in the nose cone dilator.

U.S. patent application Ser. No. 12/074,755 (Publication No. 2008/0221656) entitled "Endovascular Deployment Device" teaches radiographic marking on a nose cone dilator and the teachings therein are incorporated in their entirety herein.

Preferably the stent graft delivery device further comprises a radiopaque marking on one side of the nose cone dilator whereby the rotational position of the nose cone dilator can be observed by radiographic techniques, the pull wire being fastened to the distal end of the nose cone dilator on an opposite side of the nose cone dilator to the radiopaque marking on the nose cone dilator.

In one embodiment the wire pull mechanism comprises a winch arrangement.

Preferably the wire pull mechanism comprises a lock mechanism whereby after the wire has been pulled it can be locked in a pulled position.

The guide wire catheter can comprise a tube formed from a nickel titanium alloy metal such as that sold under the Trade mark Nitinol.

The pull wire can comprise stainless steel wire or Nitinol™ wire.

Preferably the wire pull mechanism comprises a grip associated with the handle and the grip is able to be slid along the handle to pull the pull wire. A thumb screw arrangement may be associated with the grip to lock the grip to the handle at a selected curvature of the proximal end of the delivery device as observed by radiographic techniques.

Preferably the pusher catheter comprises a proximal pusher extension comprising a sleeve extending from the pusher catheter towards the nose cone dilator guide wire catheter and the pull wire extends through the pusher extension in order to restrict the length of guide wire catheter which is caused to bend by the pulling on the pull wire.

Preferably the stent graft delivery device further includes a constricting sheath around the pusher catheter and extending to the nose cone dilator, the sheath constraining the stent graft around the guide wire catheter during introduction of the stent graft into the vasculature.

According to a further aspect of the present invention, there is provided a method of treating an aortic aneurysm including deployment of a stent graft into the thoracic arch of a patient using a device as claimed in any of claims 1 to 14.

According to a further aspect of the present invention, there is provided a method of treating an aortic aneurysm including positioning a deployment device as claimed in any of claims 1 to 14 up through the descending aorta of a patient such that the proximal end of the device extends over the thoracic arch and into the ascending aorta, and pulling the pull wire in a distal direction to bend the proximal end of the guide wire catheter between the proximal end of the pusher catheter and the distal end of the nose cone dilator.

An advantage of this invention is that there is provided a delivery device which by pulling on a pull wire from external of the patient sufficient curvature may be provided in the proximal end of the delivery device for it to more closely fit the shape of the thoracic arch and to allow a working space in the outer side of the curve of the thoracic arch, for instance.

BRIEF DESCRIPTION OF THE DRAWINGS

Preferred embodiments of the invention will now be described with reference to the accompanying drawings.

DESCRIPTION OF THE PREFERRED EMBODIMENTS

Figure 1:
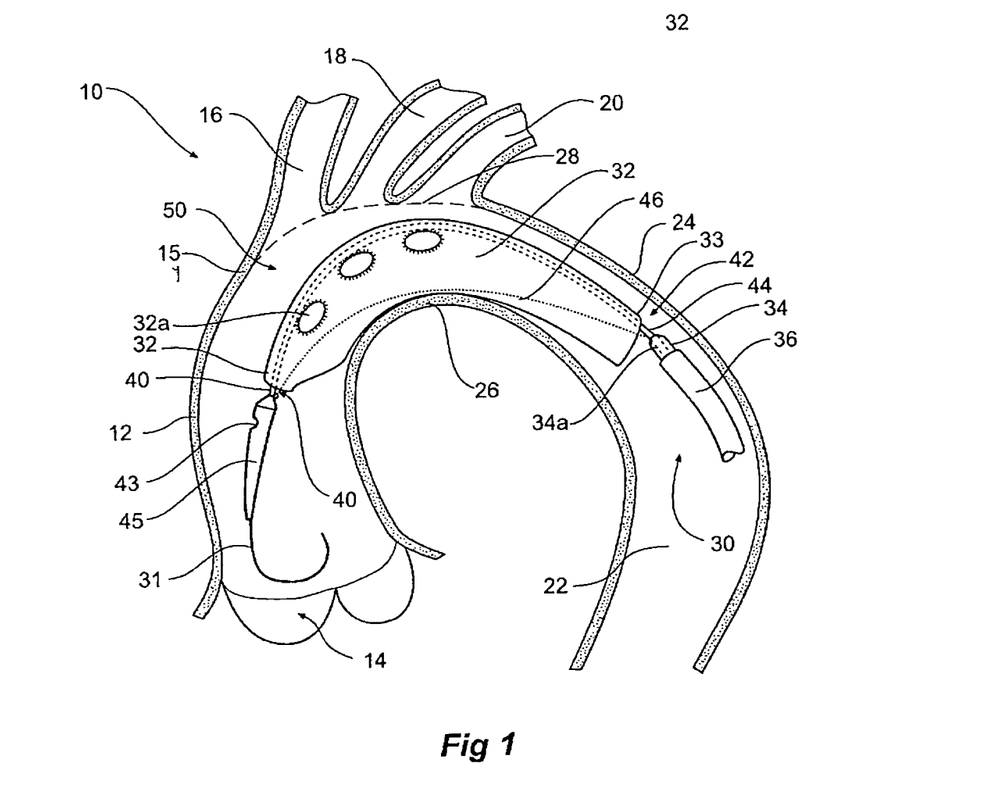
FIG. 1 shows a schematic view of the thoracic arch of a patient with a stent graft partially deployed and curved therein according to one embodiment of the present invention.

Now looking in detail at FIG. 1 which shows a schematic cross sectional view of a thoracic aorta, it will be seen that the thoracic aorta 10 comprises an ascending aorta 12 which receives blood from the heart though an aortic valve 14. At the upper end of the ascending aorta there is a thoracic arch 15 with branches for the great vessels, the inanimate artery 16, the left common carotid artery 18 and the left subclavian artery 20. The aorta after these great vessels is referred to as the descending aorta 22 and it is in this region that a thoracic aortic aneurysm can occur. In a thoracic aortic aneurysm part of the wall 24 of the descending aorta swells and can burst with serious consequences. The thoracic aortic aneurysm can extend to close to the great vessels or include the great vessels and hence it may be necessary to deploy a stent graft with side branches to extend into the great vessels. The thoracic arch has an inner side curve 26 and an outer side curve 28.

As shown in FIG. 1, a deployment device 30 has been deployed up through the descending aorta over a pre-placed guide wire 31. The proximal end of the deployment device extends over the thoracic arch and into the ascending aorta 12. A sheath 36 of the deployment device has been withdrawn to partially release the stent graft 32 but the stent graft is still retained to the deployment device at region 40 at the proximal end 31 of the stent graft 32 and at region 42 at the distal end 33 of the stent graft 32.

U.S. patent application Ser. No. 10/447,406 entitled "Trigger Wire System" teaches the use of trigger wire systems for retention of the ends of a stent graft and the teachings therein are incorporated herein in their entirety.

The stent graft 32 includes three fenestrations 32a into which are intended to be deployed side branch stents or covered stents to maintain the patency of the great vessels when the stent graft is released into the thoracic arch.

The delivery device includes a guide wire catheter 44 made from stainless steel or Nitinol™. The guide wire catheter is resilient so that it can be bent to fit the shape of the thoracic arch. The bending of the guide wire catheter can caused by engagement with the wall of the aorta and hence the curve of the delivery device would be against the outer curve 28 of the thoracic arch. As this is where the great arteries branch off from the thoracic arch this does not allow working space adjacent to the major arteries and therefore the curving mechanism of the present invention is used. Part of the pusher catheter 34 of the deployment device can be seen at the distal end of the stent graft 32. The pusher catheter has a pusher lumen 34a (see also FIG. 3) through which passes the guide wire catheter 44. The guide wire catheter 44 extending through the pusher lumen 34a is able to move longitudinally and rotationally with respect to the pusher catheter 34. The deployment device includes a nose cone dilator 45 at its proximal end and the lumen 47 of the guide wire catheter 44 extends to and through the nose cone dilator 45.

Figure 2:
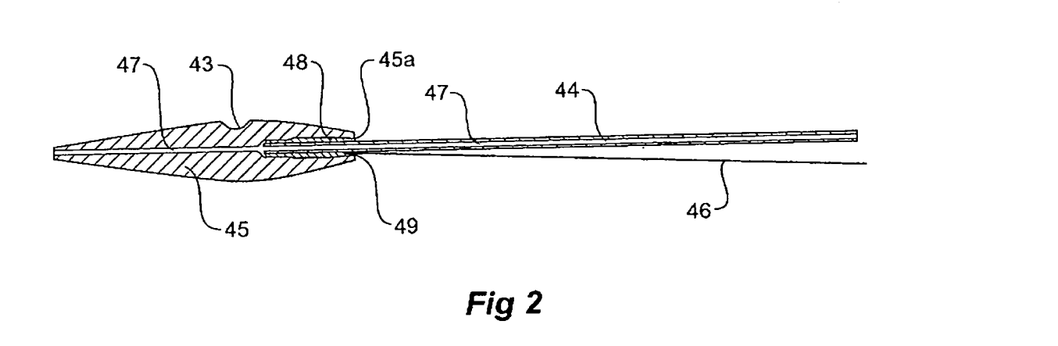
FIG. 2 shows detail of the nose cone dilator, guide wire catheter and pull wire of a delivery device according to one embodiment of the present invention.

Detail of the proximal end of the deployment device can be seen in FIG. 2. The nose cone dilator 45 is at the proximal end of the deployment device and the guide wire 44 catheter extends to and through the nose cone dilator 45. The guide wire catheter has a guide wire lumen 47 therethrough. The guide wire lumen 47 continues through the nose cone dilator 45. The nose cone dilator 45 has a notch 43 formed in it upper surface and the nose cone dilator 45 is formed from a radiopaque material such as a radiopaque polyurethane such that the orientation of the delivery device within the thoracic arch can be visualised by suitable radiographic techniques.

The curving mechanism includes a pull wire 46 which is fastened to the nose cone dilator 45 at the distal end 45a thereof where it joins to the guide wire catheter. For instance the pull wire 46 can be fastened at 49 to a sleeve 48 which is fastened such as by welding to the guide wire catheter and the nose cone dilator is fixed to the sleeve 48 by adhesive or the like. The pull wire is joined at 49 to the nose cone dilator 45 on the opposite side to the notch 43.

Referring back to FIG. 1 it can be seen that the pull wire 46 extends through the lumen of the stent graft 32 and into the pusher lumen 34a of the pusher catheter 34 (but outside the guide wire catheter 44). The pull wire then extends back to a handle of the deployment device as is discussed below and shown in FIGS. 3 to 5. Pulling on the pull wire has caused the nose cone dilator to be pulled towards the pusher catheter which has caused the guide wire catheter 44 to bend thereby forming a curve in the delivery device proximal end which more approximates the shape of the inner curve 26 of the thoracic arch and leaving some working space 50 between the stent graft and the outer curve 28 of the thoracic arch. As FIG. 1 also illustrates, when the guide wire catheter 44 is curved during use and/or deployment as a result of pulling on the pull wire 46, the curve in the guide wire catheter 44 is greater than the curve of the pull wire 46. It will be noted, too, that the notch 43 on the nose cone dilator is on the outside of the curve of the delivery device.

Figure 3:
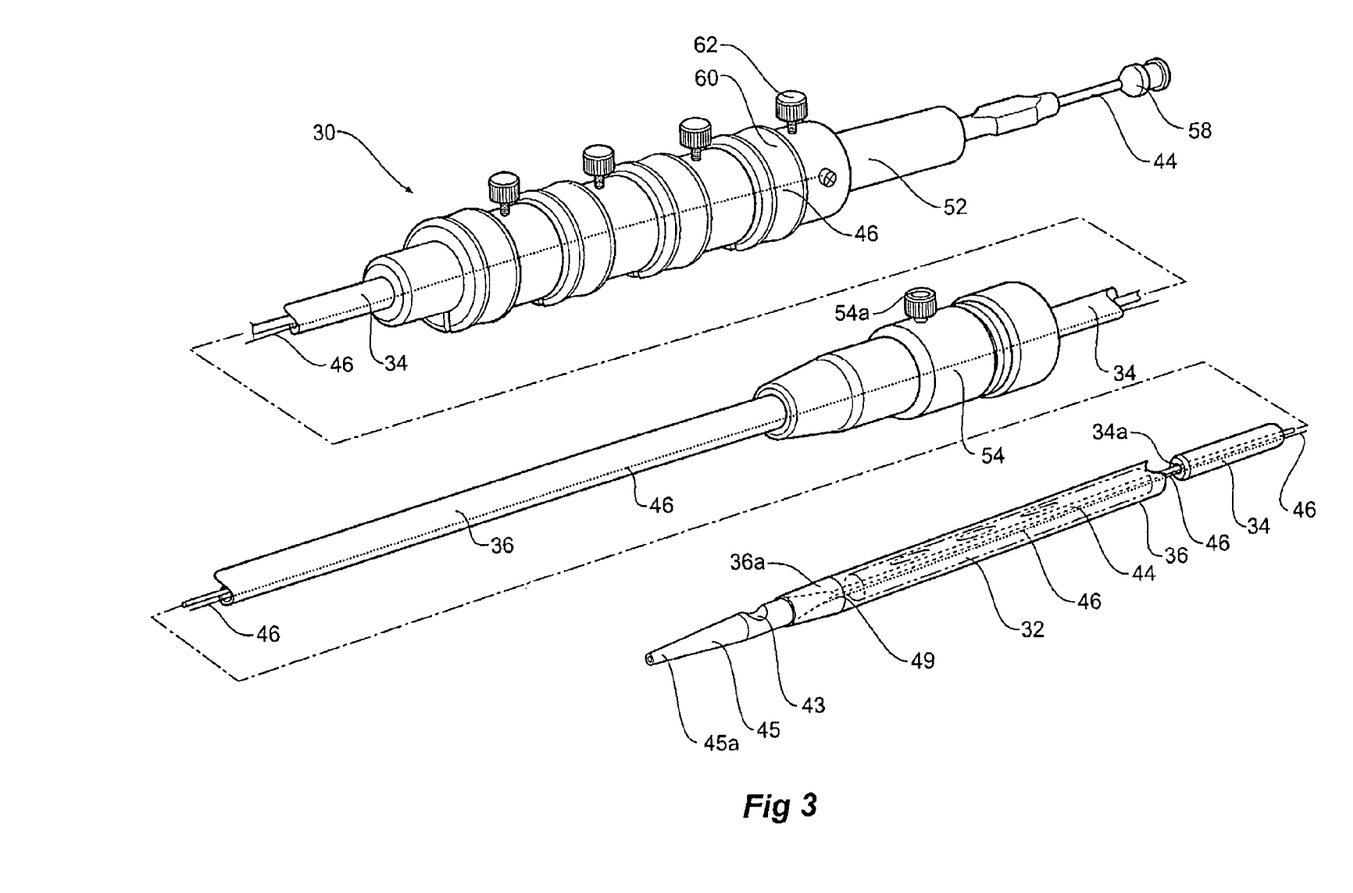
FIG. 3 shows a delivery device according to one embodiment of the present invention.
Figure 4:
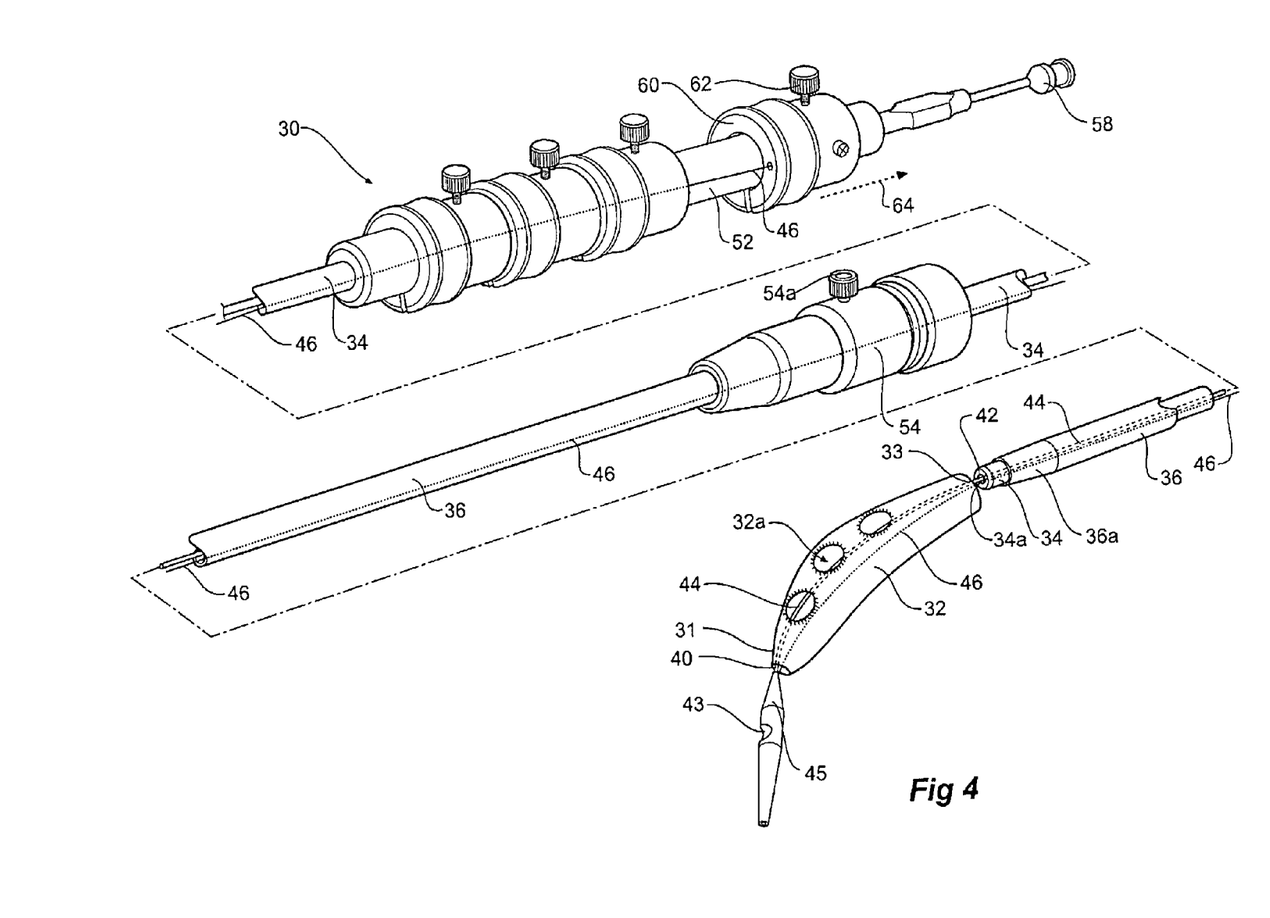
FIG. 4 shows an induced curve of the delivery device of FIG. 3.

FIGS. 3 and 4 depicts a delivery device 30 according to one embodiment of the invention. The delivery device 30 has a guide wire catheter 44 which extends from a distal handle 52 to the proximal tapered nose cone dilator 45 longitudinally through a passageway or lumen 34a of a pusher catheter 34 which is connected to the handle 52 at its distal end. An introducer sheath 36 fits coaxially around the delivery catheter 34 and extends from a tapered proximal end 36a which optionally includes a radiopaque marker to a connector valve and hub 54 attached to the distal end of the sheath. The introducer sheath 36 extends proximally to the nose cone dilator 45 and covers the stent graft 32 during introduction of the deployment device into a patient and is withdrawn distally to expose the stent graft 32 during deployment when the deployment device is in a selected position within the vasculature of a patient. The stent graft or implantable device 32 is carried on the guide wire catheter 44 proximally of the pusher catheter 34 and distally of the nose cone dilator 45. The stent graft 32 comprises a tubular body of a biocompatible material and a plurality of self expanding stents (not shown for clarity). Connector valve and hub 54 includes a silicone disk assembly (not shown) for preventing the backflow of fluids therethrough. The disk assembly includes a slit for the insertion of the nose cone dilator 45 and delivery catheter 34. Connector and hub 54 also includes side arm 54a to which a tube may be connected for introducing and aspirating fluids therethrough. Nose cone dilator 45 includes a tapered proximal end 45a for accessing and dilating a vascular access site over a well-known and commercially available wire guide (not shown).

The wire guide is inserted in the vessel with an introducer needle using, for example, the well-known percutaneous vascular access Seldinger technique. A well-known male Luer lock connector hub 58 is attached at the distal end of the guide wire catheter 44 for connection to syringes and other medical apparatus. The handle 52 at the distal end of the pusher catheter 34 remains outside a patient in use and carries the trigger wire release handle mechanisms used to release the various portions of the stent graft. The proximal end the stent graft 32 is retained on the delivery device by the use of trigger wires (not shown) connected to one of the release handles, the distal end of the stent graft is retained on the delivery device by the use of trigger wires (not shown) connected to another the release handles. The handle also includes a release to mechanism for a release wire for diameter reducing ties (not shown) for the stent graft.

The pull wire 46 extends from where it is fastened to the distal end of the nose cone dilator 45 (see FIG. 2) through the lumen 34a of the stent graft 32 and into the pusher lumen of the pusher catheter 34. The pull wire then extends back to a handle 52 of the deployment device where it is fastened to pull wire grip 60 which can be clamped to the handle by thumb screw 62. As can be seen on FIG. 4 pulling on the grip 60 in the distal direction as shown by the arrow 64 causes the pull wire 46 to bend the proximal end of the guide wire catheter between the proximal end of the pusher catheter 34 and the distal end of the nose cone dilator 45 to form the curve as shown. This also bends the stent graft into a corresponding shape. When the pull wire 46 is pulled to bend the guide wire catheter 44, the pull wire 46 remains relatively taut as shown in FIGS. 1 and 4, such that the guide wire catheter 44 forms a curve that is greater than a curve formed in the pull wire 46. This may provide for an increased range of motion and movement of the curved portion of the guide wire catheter 44, thereby facilitating bending of the delivery device to more closely fit the shape of a portion of the vasculature of a patient into which the device is deployed. Once the desired curvature has been obtained as can be seen by suitable radiographic techniques the thumb screw 62 can be used to clamp the grip 60 to the handle to hold the curvature during subsequent stages of the introduction procedure. At this stage the stent graft 32 is still retained on the deployment device at region 40 at the proximal end 31 of the stent graft and at region 42 at the distal end of the stent graft.

Subsequent stages of the introduction procedure can include catheterization of the fenestrations and introduction of a suitable side arm delivery device but before actual deployment of the side arms the pull wire can be released and the stent graft released from the delivery device. This would ensure that a side arm is not dislodged when the main stent graft settles into its final position in the thoracic arch.

Figure 5:
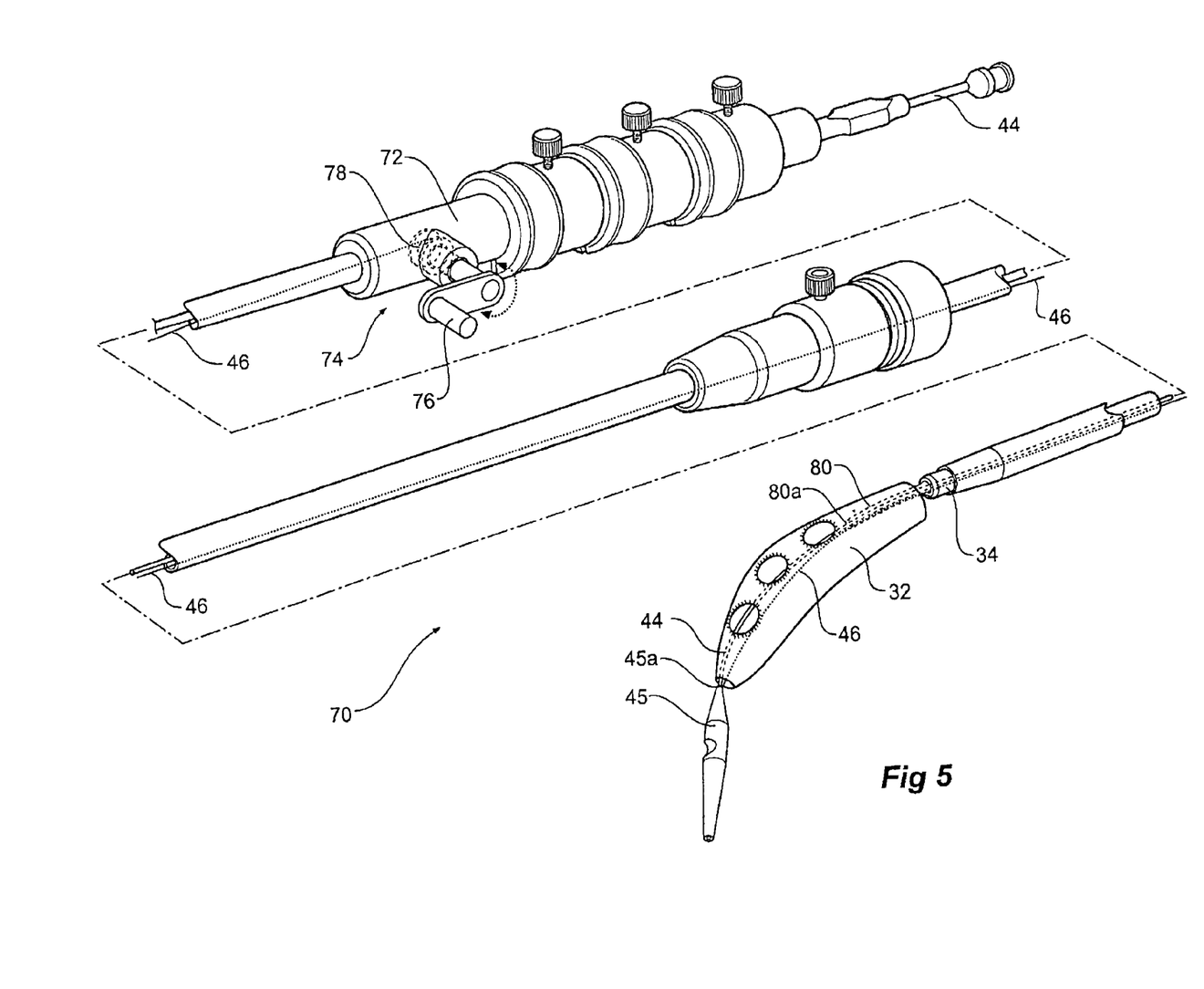
FIG. 5 shows a delivery device according to another alternative embodiment of the present invention.

FIG. 5 shows an alternative embodiment of delivery or deployment device according to the present invention. In this embodiment the same reference numerals are used for items corresponding to those in FIGS. 3 and 4.

The delivery device 70 of this embodiment has two variations from the earlier embodiment. First there is a winch arrangement for pulling the pull wire and second there is a pusher extension to reduce the amount of the guide wire catheter which is caused to bend by pulling on the pull wire. These two variations need not be used together and could be applied separately.

In this embodiment the handle 72 of the deployment device 70 has a winch assembly 74 which includes a winding handle 76 connected to a winch drum 78 within the winch assembly 74 and the pull wire is wound around the winch drum 78. The winch arrangement includes a releasable locking mechanism (not shown) to hold the winch drum in a selected rotational position.

At the proximal end of the pusher catheter 34 is a catheter extension 80 through which passes the guide wire catheter 44 and the pull 46 wire parallel to but outside the guide wire catheter. The catheter extension 80 extends part way into the lumen of the stent graft 32. This restricts the length of guide wire catheter which is bent by the pulling on the pull wire.

Rotating the winding handle 76 causes the pull wire 46 to bend the proximal end of the guide wire catheter between the proximal end 80a of the pusher catheter extension 80 and the distal end 45a of the nose cone dilator 45 to form the curve as shown in FIG. 5. Once the desired curvature has been obtained as can be seen by suitable radiographic techniques the releasable locking mechanism holds the curvature.

The winch assembly can be placed on other parts of the handle 72.

Throughout this specification various indications have been given as to the scope of the invention but the invention is not limited to any one of these but may reside in two or more of these combined together. The examples are given for illustration only and not for limitation.

The invention claimed is:

1. A stent graft delivery device comprising:
a nose cone dilator at a proximal end of the device,
a resilient guide wire catheter extending from a distal end of the device to and through the nose cone dilator,
a pusher catheter extending from the distal end of the device towards the proximal end,
a stent graft retained on the delivery device between the distal end of the nose cone dilator and the pusher catheter, the stent graft having a graft lumen therethrough and wherein the guide wire catheter extends through the graft lumen and through the pusher catheter,
a pull wire fastened at or adjacent the distal end of the nose cone dilator such that when the guide wire catheter is curved during deployment, the pull wire is fastened on the inside of the curve, said pull wire extending distally and adjacent to and outside the guide wire catheter and through the stent graft lumen and the pusher catheter towards the distal end of the device, and
a wire pull mechanism at or adjacent the distal end of the device operable to pull the pull wire to induce a curve in the guide wire catheter distally of the nose cone dilator, wherein when the guide wire catheter is curved during deployment, the curve of the guide wire catheter is greater than a curve of the pull wire.

2. A stent graft delivery device as in claim 1 further comprising a radiopaque marking on one side of the nose cone dilator whereby the rotational position of the nose cone dilator can be observed by radiographic techniques.

3. A stent graft delivery device as claimed in claim 2 wherein the pull wire is fastened at or adjacent the distal end of the nose cone dilator on an opposite side of the nose cone dilator to the radiopaque marking.

4. A stent graft delivery device as in claim 1 wherein the wire pull mechanism comprises a lock mechanism to lock the wire in a pulled position.

5. A stent graft delivery device as in claim 1 wherein the wire pull mechanism comprises a winch arrangement.

6. A stent graft delivery device as in claim 5 wherein the winch arrangement includes a winding handle connected to a winch drum and a releasable locking mechanism to hold the winch drum in a selected rotational position.

7. A stent graft delivery device as in claim 1 wherein the guide wire catheter comprises a tube formed from a nickel titanium alloy.

8. A stent graft delivery device as in claim 1 wherein the nose cone dilator is formed from a radiopaque material and the radiographic marking comprises the nose cone dilator being of a selected transverse profile whereby the nose cone dilator can be observed by radiographic means during an endovascular procedure to be in a selected rotational orientation.

9. A stent graft delivery device as in claim 8 wherein the nose cone dilator is formed from a radiopaque material and the radiographic marking comprises a notch in the nose cone dilator.

10. A stent graft delivery device as in claim 1 wherein the pull wire comprises stainless steel wire or a nickel titanium alloy wire.

11. A stent graft delivery device as in claim 1 further comprising a handle at the distal end of the device and wherein the wire pull mechanism comprises a grip associated with the handle and a thumb screw arrangement associated with the grip such that the grip is slideable along the handle to pull the pull wire and the thumb screw is operable to lock the grip to the handle once the proximal end of the delivery device is at a selected curvature.

12. A stent graft delivery device as in claim 1 wherein the pusher catheter comprises a proximal pusher extension comprising a sleeve extending from the pusher catheter towards the nose cone dilator and part way into the stent graft, the pull wire extending through the pusher extension.

13. A stent graft delivery device as in claim 1 further including a constricting sheath around the pusher catheter and extending to the nose cone dilator, the sheath constraining the stent graft around the guide wire catheter during introduction of the stent graft into the vasculature.

14. A stent graft delivery device comprising a handle at a distal end, a nose cone dilator at a proximal end, the nose cone dilator including a distal end, a guide wire catheter extending from the handle to and through the nose cone dilator at the proximal end, the guide wire catheter being constructed from a resilient and flexible material, a pusher catheter extending from the handle towards the proximal end, a stent graft retained on the delivery device between the distal end of the nose cone dilator and the pusher catheter, the stent graft having a graft lumen therethrough and the guide wire catheter extending through the graft lumen, a pusher lumen through the pusher catheter, the guide wire catheter extending through the pusher lumen and able to move longitudinally and rotationally with respect to the pusher, a pull wire fastened to the distal end of the nose cone dilator and the pull wire extending distally and adjacent to and outside the guide wire catheter and through the stent graft lumen and the pusher lumen to the handle and a wire pull mechanism for the pull wire associated with the handle, whereby the pull wire can be pulled by the wire pull mechanism to induce a curve in the guide wire catheter distally of the nose cone dilator such that the proximal end of the delivery device more closely fits the shape of a portion of the vasculature of a patient into which the device is deployed, wherein when the guide wire catheter is curved during deployment, the curve of the guide wire catheter is greater than a curve of the pull wire.

* * * * *